US012514575B2

(12) United States Patent
Collazo

(10) Patent No.: US 12,514,575 B2
(45) Date of Patent: Jan. 6, 2026

(54) ANATOMICAL JOINT DISTRACTOR

(71) Applicant: Howmedica Osteonics Corp., Mahwah, NJ (US)

(72) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 429 days.

(21) Appl. No.: 17/989,915

(22) Filed: Nov. 18, 2022

(65) Prior Publication Data

US 2023/0157680 A1 May 25, 2023

Related U.S. Application Data

(60) Provisional application No. 63/281,142, filed on Nov. 19, 2021.

(51) Int. Cl.
*A61B 17/02* (2006.01)

(52) U.S. Cl.
CPC .... *A61B 17/025* (2013.01); *A61B 2017/0268* (2013.01)

(58) Field of Classification Search
CPC ... A61B 17/025; A61B 17/1659; A61B 17/02; A61B 17/0218
See application file for complete search history.

(56) References Cited

U.S. PATENT DOCUMENTS 5,334,194 A 8/1994 Mikhail
5,735,904 A 4/1998 Pappas
6,632,225 B2 10/2003 Sanford et al.
6,969,393 B2 * 11/2005 Pinczewski ........ A61B 17/1659 606/88
7,371,240 B2 5/2008 Pinczewski et al.
8,092,462 B2 1/2012 Pinczewski et al.
8,167,888 B2 5/2012 Steffensmeier
8,303,596 B2 11/2012 Plaβky et al.
8,323,287 B2 12/2012 Pinczewski et al.
8,690,882 B2 4/2014 Pinczewski et al.
8,998,911 B2 4/2015 Wilkinson et al.
9,439,660 B2 9/2016 Pinczewski et al.
9,463,032 B2 10/2016 Fox
9,504,480 B2 11/2016 Marik et al.
9,675,471 B2 6/2017 Bojarski et al.
9,750,511 B2 9/2017 Goodfellow et al.
10,307,172 B2 6/2019 Sikora et al.
10,959,717 B2 3/2021 Sehat
(Continued)

FOREIGN PATENT DOCUMENTS

WO 2012024306 A2 2/2012
WO 2021029984 A1 2/2021

*Primary Examiner* — Si Ming Ku
(74) *Attorney, Agent, or Firm* — Lerner David LLP

(57) ABSTRACT

A knee joint distractor includes a handle that has a length that extends along a longitudinal axis of the knee joint distractor and a distraction head connected to the handle. The distraction head has a femoral contact side and a tibial contact side. The femoral contact side has a first femoral contact portion. The tibial contact side has first and second tibial contact portions. The first tibial contact portion defines an inferior apex of the tibial contact side. The second tibial contact portion has a plurality of teeth offset from the inferior apex in a direction toward the handle.

18 Claims, 5 Drawing Sheets

(56) References Cited

U.S. PATENT DOCUMENTS

| | | | | |
|---|---|---|---|---|
| 11,116,647 | B2 * | 9/2021 | Greenhalgh | A61F 2/4601 |
| 11,154,289 | B2 | 10/2021 | Schussler | |
| 11,642,117 | B2 | 5/2023 | Nguyen et al. | |
| 2006/0111726 | A1 * | 5/2006 | Felt | A61F 2/4657 623/20.14 |
| 2014/0222006 | A1 | 8/2014 | Pinczewski et al. | |
| 2018/0185166 | A1 | 7/2018 | Johannaber | |
| 2020/0155205 | A1 * | 5/2020 | Tanaka | A61B 17/1757 |
| 2021/0205044 | A1 | 7/2021 | Nguyen et al. | |
| 2021/0361273 | A1 | 11/2021 | Jaramaz et al. | |

* cited by examiner

ANATOMICAL JOINT DISTRACTOR

CROSS-REFERENCE TO RELATED APPLICATIONS

This application claims the benefit of the filing date of U.S. Provisional Application No. 63/281,142, filed Nov. 19, 2021, the disclosure of which is hereby incorporated by reference.

BACKGROUND OF THE INVENTION

Total knee arthroplasty ("TKA") or total knee replacement is a common orthopedic procedure in which damaged or diseased articular cartilage and/or bone of the knee is replaced with prosthetic components. Prior to implanting such prosthetic components, a surgeon generally resects a portion of the patient's native bone to receive an associated prosthesis. For example, a surgeon might make one or more planar cuts at a distal end of a femur and proximal end of a tibia so that corresponding surfaces of femoral and tibial prosthetic components can be respectively attached thereto.

Prior to making such resections, the joint laxity of the native knee is often assessed to help determine the depth and orientation of the resections to be made. One common technique of assessing joint laxity in the native knee prior to bone resection is to pry the joint apart to ascertain the degree to which the joint opens and the amount of force needed to do so. This is, of course, a subjective tactile assessment based on surgeon experience.

Two commonly used devices to pry the knee joint apart are an osteotome, and a spoon tensioner. Osteotomes, such as the one shown in FIG. 1A, are like a carpenter's wood chisel in that they are specifically designed to cut hard tissue, such as bone or cartilage by impaction. All knee replacement procedures have osteotomes readily available as part of the standard instrumentation that is brought into the operating theater. It is almost certain that the repurposed use of an osteotome to distract the joint arose through surgeon improvisation by having a narrow and thin instrument within easy reach. The spoon tensioner, such as the one shown in FIG. 1B, is colloquially named for its similarity to the eating utensil and is an attempt to create a device for the express purpose of distracting the knee joint.

Although commonly used for the purpose of assessing joint laxity, such instruments fall well short of being effective at fulfilling the desired functionality. At least one reason such instruments are inadequate has to do with their shape. Native femoral condyles and tibial condyles are respectively convex and concave in the sagittal and coronal planes. Placing any device within the joint space that is flat in at least one of the two said planes creates an ill-fitting and unstable construct. As shown, the osteotome is flat in both the sagittal and coronal planes, notwithstanding that it is dangerously sharp. The spoon tensioner, while being slightly curved in the coronal plane, is nonetheless flat in the sagittal plane. Additionally, both devices have smooth contacting surfaces as well as constant proximal/distal thicknesses. When placed in the joint space, any flexion/extension movement of the leg tends to eject, or "spit" out the instrument, which results in extra work and time for the surgeon. This is exacerbated by the fact that these instruments are used prior to any bone resection, meaning that they are inserted into a joint space partially covered in cartilage and synovium fluid, resulting in a very low friction, slippery environment. Therefore, further improvements are desirable.

BRIEF SUMMARY OF THE INVENTION

In one aspect of the present disclosure, a knee joint distractor includes a handle that has a length that extends along a longitudinal axis of the knee joint distractor and a distraction head connected to the handle and extending therefrom. The distraction head has a femoral contact side and a tibial contact side. The femoral contact side has a first femoral contact portion. The tibial contact side gas first and second tibial contact portions. The first tibial contact portion defines an inferior apex of the tibial contact side. The second tibial contact portion has a plurality of teeth offset from the inferior apex in a direction toward the handle.

Additionally, the teeth may each extend in a direction transverse to the longitudinal axis of the knee joint distractor. The length of each tooth may be interrupted by a recessed channel. Each tooth may include a first and second edge disposed at opposing sides of the recessed channel. Also, each tooth may include a third and fourth edge disposed at respective opposed ends thereof.

Continuing with this aspect, the tibial contact side may be curved in a sagittal plane such that it defines an arc length having a first radius of curvature. The first tibial contact portion may have a curved surface that is congruent with the arc length in the sagittal plane. The curved surface of the first tibial contact portion may be curved in a coronal plane orthogonal to the sagittal plane. Each tooth may have a sagittal plane profile that extends no further than the arc length. The sagittal profile of each tooth may be congruent with the arc length.

Furthermore, the first femoral contact portion may be concavely curved in sagittal and coronal planes. The femoral contact side includes a second femoral contact portion that is convexly curved in the coronal plane. The distractor of claim 12, wherein the second femoral contact portion is concavely curved in the sagittal plane. The distractor of claim 1, wherein the distractor head has first and second ends and is tapered such that a thickness measured between the femoral and tibial contact sides increases from the first end to the second end, the second end being connected to the handle.

In another aspect of the present disclosure, a knee joint distractor includes a handle that has a length that extends along a longitudinal axis of the knee joint distractor and a distraction head that is connected to the handle and extends therefrom. The distraction head has a femoral contact side and a tibial contact side. The femoral contact side has a first femoral contact portion. The tibial side has first and second tibial contact portions and an arc length defined by at least the first tibial contact portion that has a first radius of curvature. The second tibial contact portion has a plurality of teeth bounded by the arc length such that the teeth do not extend radially beyond the arc length.

Additionally, each tooth of the plurality of teeth may have a radial profile congruent with the arc length. The radial profile of each tooth may be convexly curved in a sagittal plane and a coronal plane. The teeth may each extend in a direction transverse to the longitudinal axis of the knee joint distractor. The length of each tooth may be interrupted by a recessed channel. Each tooth may include a first and second edge disposed at opposing sides of the recessed channel. Each tooth may include a third and fourth edge disposed at respective opposed ends thereof.

Continuing with this aspect, the tibial contact side may be curved in a sagittal plane such that it defines an arc length having a first radius of curvature. The first tibial contact portion may have a curved surface that is congruent with the arc length in the sagittal plane. The curved surface of the first tibial contact portion may be curved in a coronal plane orthogonal to the sagittal plane. Each tooth may have a sagittal plane profile that extends no further than the arc length.

Furthermore, the first femoral contact portion may be concavely curved in sagittal and coronal planes. The femoral contact side may include a second femoral contact portion that is convexly curved in the coronal plane. The second femoral contact portion may be concavely curved in the sagittal plane. The distractor head may have first and second ends and may be tapered such that a thickness measured between the femoral and tibial contact sides increases from the first end to the second end. The second end may be connected to the handle.

In an even further aspect of the present disclosure, a knee joint distractor includes a handle that has a length extending along a longitudinal axis of the knee joint distractor and a distraction head connected to the handle. The distraction head has a femoral contact side that has first and second femoral contact portions and a tibial contact side that has a first tibial contact portion. The first femoral contact portion is concavely curved in a coronal plane, and the second femoral contact portion is convexly curved in the coronal plane.

In a still further aspect of the present disclosure a knee joint distractor includes a handle that has a length extending along a longitudinal axis of the knee joint distractor and a distraction head connected to the handle. The distraction head has a femoral contact side and a tibial contact side. The femoral contact side has a first femoral contact portion concavely curved in a sagittal plane and a coronal plane. The tibial contact side has first and second tibial contact portions convexly curved in the sagittal and coronal planes. The second contact portion has a plurality of teeth.

BRIEF DESCRIPTION OF THE DRAWINGS

The features, aspects, and advantages of the present invention will become better understood with regard to the following description, appended claims, and accompanying drawings in which:

DETAILED DESCRIPTION

Figure 1A:
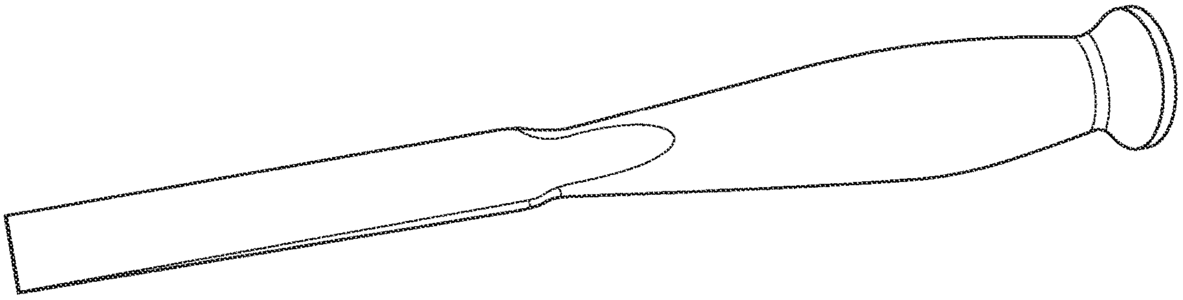
FIG. 1A (Prior Art)
FIG. 1A is a perspective view of a prior art osteotome.

As used herein unless stated otherwise, the term "proximal" means closer to the heart, and the term "distal" means further from the heart. The term "anterior" means toward the front part of the body or the face, the term "posterior" means toward the back of the body. The term "medial" means closer to or toward the midline of the body, and the term "lateral" means further from or away from the midline of the body. The term "inferior" means closer to or toward the feet, and the term "superior" means closer to or toward the crown of the head.

FIGS. 2A-2D depict a joint distractor 10 according to an embodiment of the present disclosure. Joint distractor 10 generally includes a handle or shank 20 and a distraction head 30.

Handle 20 includes a first portion or grip portion 22 and a second portion or intermediate portion 26. Thus, first portion 22 is generally gripped by a surgeon and can have a variety of ergonomic shapes to comfortably fit in a hand. In the embodiment shown, first portion 22 is elongate with a generally rectangular cross-section. In other embodiments, first portion 22 may have finger grooves and the like that are configured to conform to the surgeon's hand. First and second portions 22, 26 are delineated from each other by a hand stop 24, which in the embodiment depicted is in the form of dual projections extending sideways from joint distractor 10.

Second portion 26 is intermediate first portion 22 and distraction head 30. Second portion 26 has a reduced superior to inferior (S-I) or top to bottom thickness as compared to first portion 22. This reduction in thickness is created by a cutout or recess 27 that forms a clearance space for an anterior tibia as the joint distractor 10 is used in a knee joint space, as described further below. It is noted that, although first and second portions 22, 26 are shown as having the same orientation along a longitudinal axis of distractor 10, second portion 26 may be canted relative to first portion 22 depending on the circumstances and/or surgeon preference. For example, second portion 26 may be canted inferiorly or superiorly such that first and second portions 22, 26 form an oblique angle therebetween to provide the surgeon with a different feel or leverage.

Distraction head 30 extends from handle 20 and generally has a femoral bone contact side 31 and a tibial bone contact side 32. Femoral and tibial bone contact sides 31, 32 are configured to conform to corresponding lateral and/or medial condyles of a femur 50 and a tibia 60, as shown in FIG. 3A, and to provide anti-skid characteristics that allow joint distractor 10 to distract the joint space between these bones without slippage or being ejected out of such joint space.

Figure 2A:
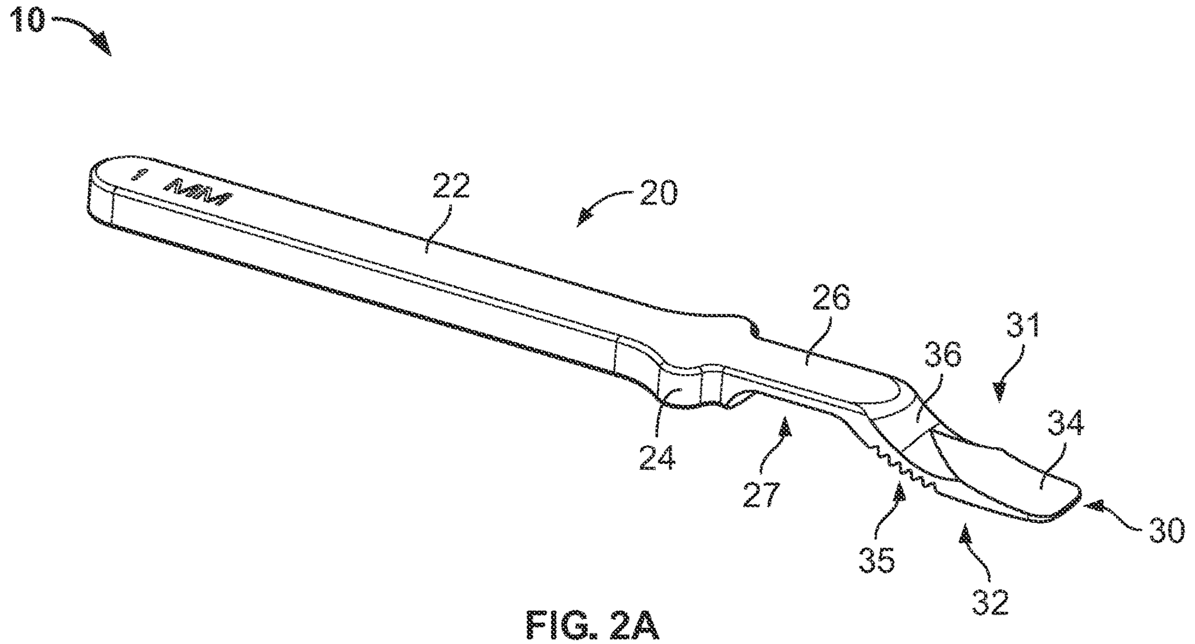
FIG. 2A is a perspective view of a joint distractor according to an embodiment of the present disclosure.
Figure 2B:
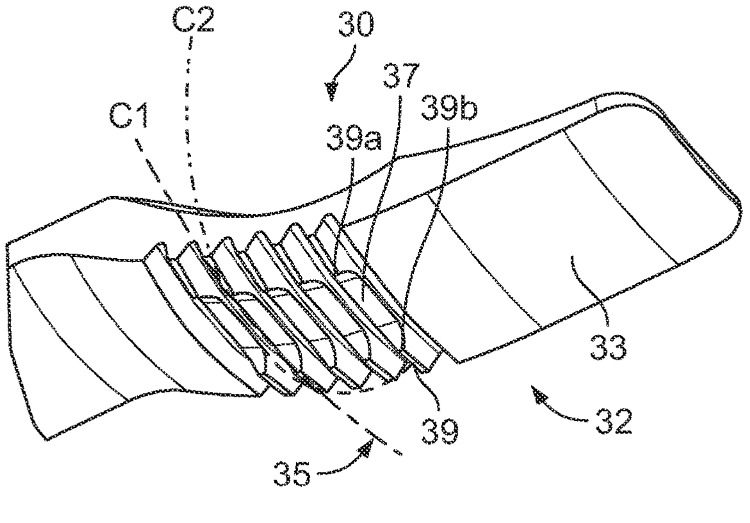
FIG. 2B is a partial bottom perspective view of the joint distractor of FIG. 2A.
Figure 2C:
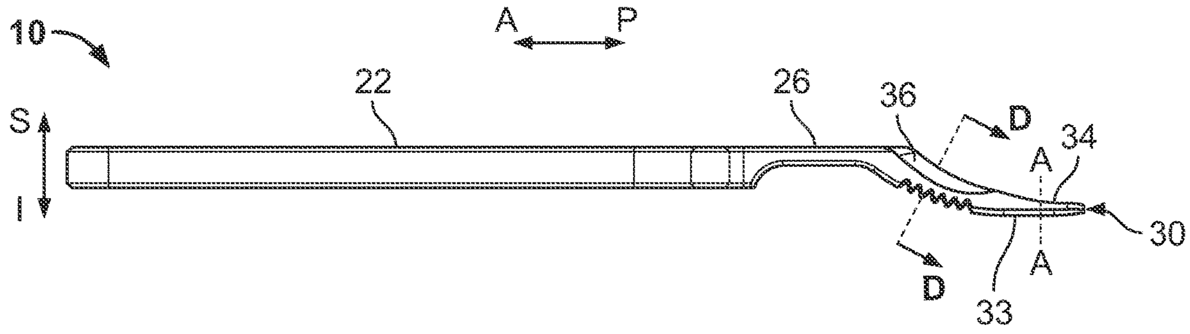
FIG. 2C is a side view of the joint distractor of FIG. 2A.
Figure 3A:
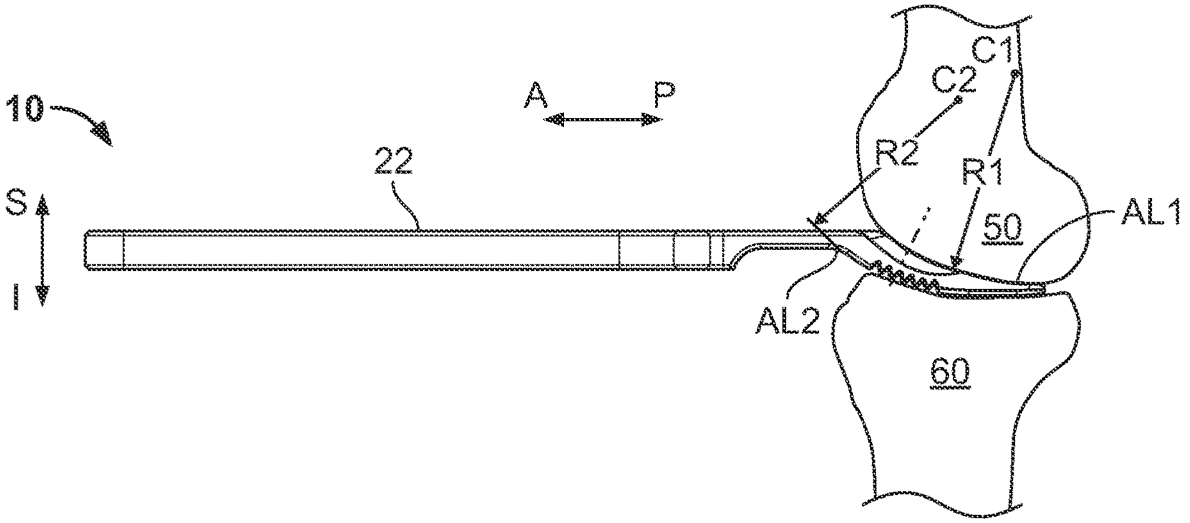
FIGS. 3A-3C depict application of the joint distractor of FIG. 2A to a knee joint.

As shown in FIGS. 2C and 3A, femoral and tibial contact sides 31, 32 are each curved in a first plane or sagittal plane such that each side 31, 32 defines an arc length that has a radius of curvature. Femoral bone contact side 31 has a first arc length AL1 that has a first radius of curvature R1, and tibial bone contact side 32 has a second arc length AL2 that has a second radius of curvature R2, as shown in FIG. 3A. The centers of curvature C1, C2 for each side 31, 32 are offset from each other in the sagittal plane in both an anteroposterior direction and a superior-inferior direction. More specifically, the center of curvature C2 of AL2 is positioned anteriorly and inferiorly to the center of curvature C1 of AL1. In the embodiment depicted, R1 is greater than R2. For example, R1 may be 1.50 in. and R2 may be 1.32 in. Although R1 is greater than R2, the offset position of C1 and C2 causes AL1 and AL2 to be divergent such that the thickness of distraction head 30 increases in a posterior to anterior direction to form a posterior to anterior expanding taper. In other words, a thickness of distraction head 10, which is defined between femoral and tibial bone contact sides 31, 32, increases from a first end of distraction head 10 to a second end of distraction head 10. The second end of distraction head 10 is connected to handle 20. This taper helps facilitate insertion of distraction head 30 into a joint space, as best shown in FIG. 3A.

Figure 2D:
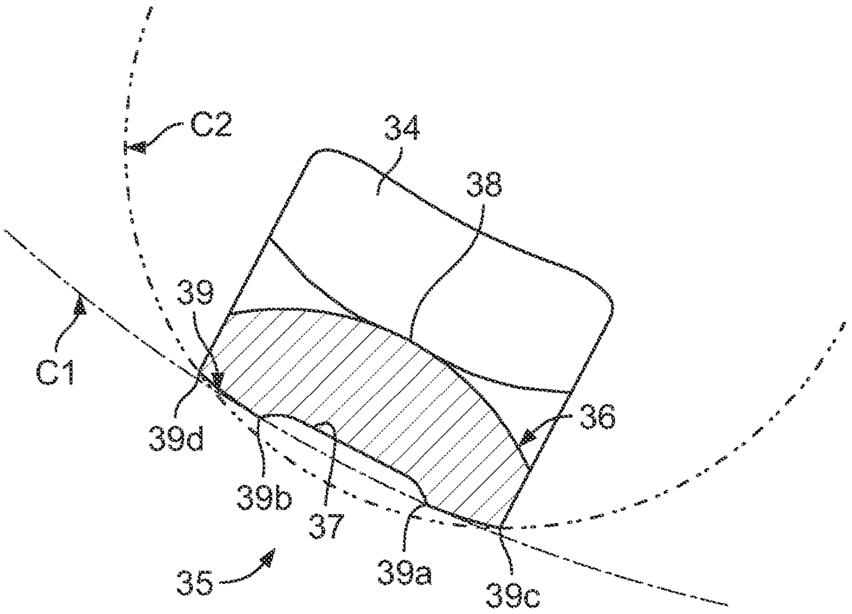
FIG. 2D is a cross-sectional view of the joint distractor of FIG. 2CA taken along line D-D thereof.

Femoral contact side 31 includes a first femoral contact portion 34 and a second femoral contact portion 36. AL1 spans the respective lengths of first and second femoral contact portions 34, 36 and is generally congruent with at least first or second femoral contact portions 34, 36, but preferably congruent with both. In this regard, AL1 is defined at least by first femoral contact portion 34, but preferably also second femoral contact portion 36. First femoral contact portion 34 is in the form of a concavely curved surface which is curved in the sagittal plane such that it is congruent with AL1. Thus, the sagittal curvature of first femoral contact portion 34 has a radius of curvature equal to R1 of AL1. First femoral contact portion 34 is also concavely curved in a coronal plane, as shown in FIG. 2D.

Figure 3B:
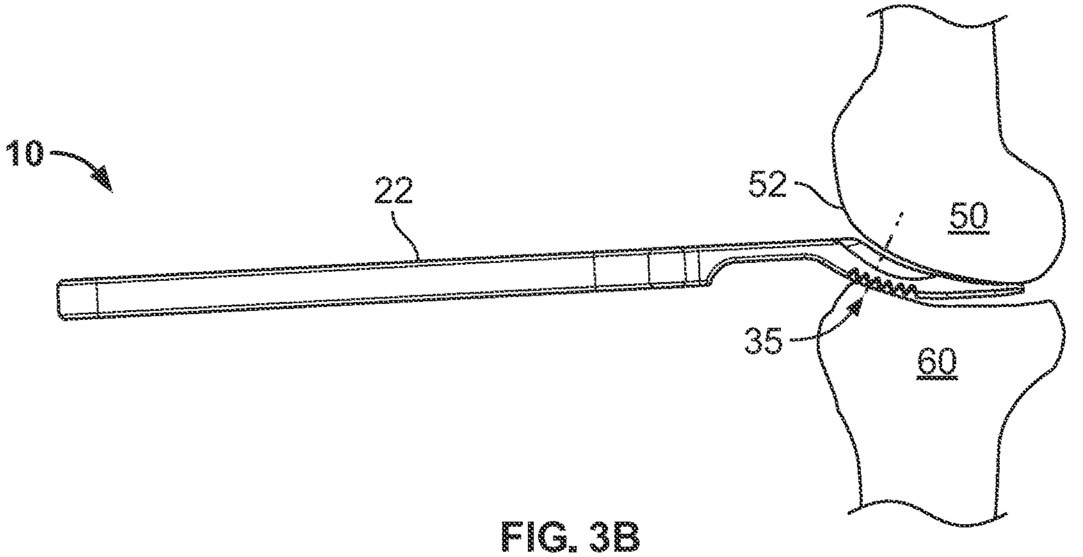
Figure 3C:
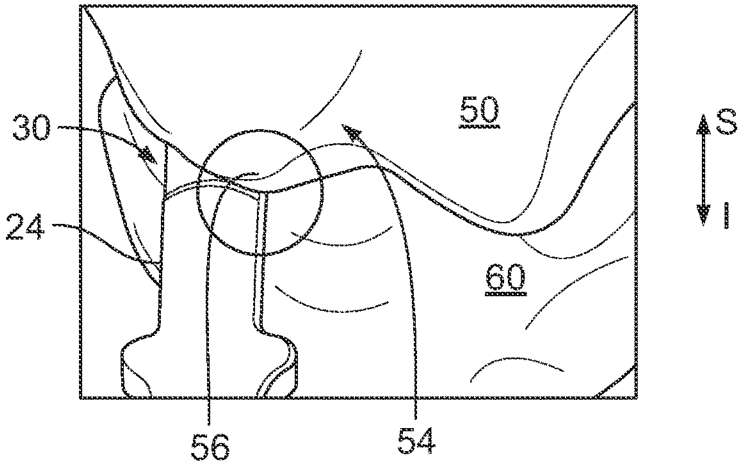

Second femoral contact portion 36 extends from first femoral contact portion 34 toward handle 20 and is in the form of a saddle shape surface. In this regard, second femoral contact portion 36 is concavely curved in the sagittal plane, as shown in FIG. 2C, while being convexly curved in the coronal plane, as shown in FIG. 2D. In the coronal plane, second femoral contact portion 36 has a crest or ridge 38 located at about the midline of distraction head 30 which forms the highest point of second femoral contact portion 36, whereas the lowest points of second femoral contact portion 36 are located at opposing sides of distraction head 30. Ridge 38 follows the sagittal curvature of femoral contact side 31 and is therefore congruent with AL1 just as first femoral contact portion 34. However, as indicated above, in some embodiments only first femoral contact portion 34 may be congruent and therefore may only define AL1. In the embodiment depicted in which there is congruency between each of first and second femoral contact portions 34, 36, there is a seamless transition from first femoral contact portion 34 to second femoral contact portion 36. This transition can be seen in FIG. 2A in which first and second femoral contact portions 34, 36 intersect at a triangular interface. The saddle shaped configuration of second femoral contact portion 36 provides clearance with an anterior prominence 56 of a trochlear groove 54 of femur 50, as illustrated in FIG. 3C.

Tibial contact side 32 includes a first tibial contact portion 33 and a second tibial contact portion 35. AL2 spans the respective lengths of first and second tibial contact portions 33, 35 and is generally congruent with at least first or second femoral contact portions 33, 35, but preferably congruent with both. In this regard, AL2 is defined by first tibial contact portion 33, but preferably also second femoral contact portion 35. First tibial contact portion 33 is in the form of a convexly curved surface which is curved in the sagittal plane and is congruent with AL2. Thus, the sagittal curvature of first tibial contact portion 33 has a radius of curvature equal to R2 of AL2. First tibial contact portion 33 is also convexly curved in the coronal plane, such that first tibial contact portion 33 has a dual convexity that defines the most inferior point of distraction head 10 relative to a longitudinal axis of handle 20. This most inferior point is referred to as the inferior apex and is intersected by axis A-A in FIG. 2C.

Second tibial contact portion 35 extends from first tibial contact portion 33 toward handle 20 and is also convexly curved in the sagittal plane and coronal plane such that it also has a dual convexity. Second tibial contact portion 35 is generally positioned offset from the inferior apex in a direction toward handle 20 and is located on an upslope from first tibial contact portion 33. This allows first tibial contact portion 33 to contact a sulcus of a tibial condyle which second tibial contact portion 35 can engage sloped wall of the tibial condyle rising from the sulcus, which helps provide anterior-posterior resistance to movement particularly since second tibial contact portion has anti-slip properties.

Second tibial contact portion 35 includes a plurality of teeth or serrations 39 arranged or arrayed along a length thereof. Teeth 39 each have a length that extends in a lateral-medial direction, as best shown in FIG. 2B. In the embodiment depicted, a recessed channel 37 interrupts the lateral-medial span of each tooth 39. This interruption forms inner edges 39*a, b* at opposite sides of recessed channel 37, as shown in FIG. 2D. Additionally, each tooth 39 has outer edges 39*c, d* formed at its terminal ends. This configuration enables each tooth 39 to engage a tibia with at least two points of contact regardless of the radius value of the coronal curvature of a tibial condyle within which distraction head 30 is positioned. For example, FIG. 2D depicts representative curvatures C1 and C2 of two differently sized tibial condyles. As shown, each tooth 39 contacts the larger curvature C1 at two nearer inner edges 39*a, b* while each tooth 39 contacts the smaller curvature C2 at two points located nearer outer edges 39*c, d*. Thus, regardless of the radius of curvature of the tibial condyle, contact should occur at a point between inner and outer edges 39*a, c* and inner and outer edges 39*b, d*.

Figure 1B:
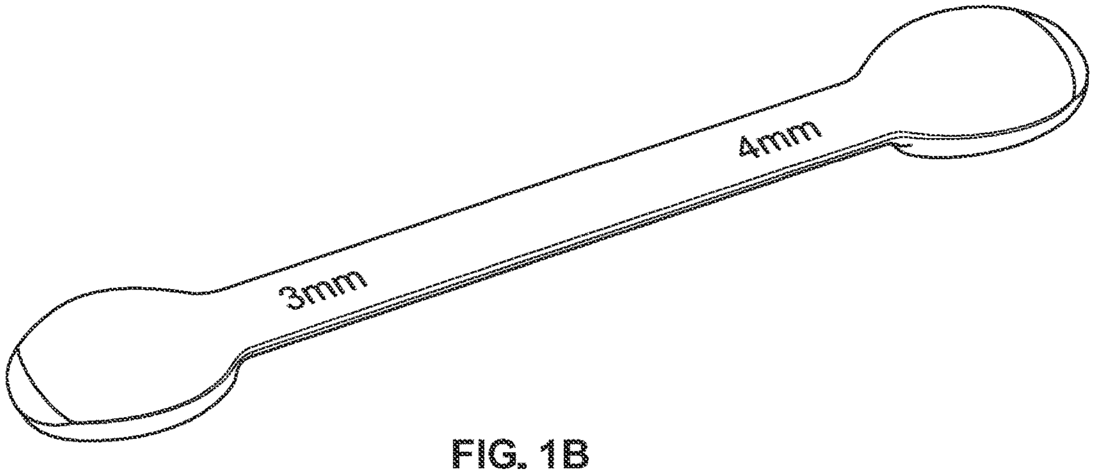
FIG. 1B (Prior Art)
FIG. 1B is a perspective view of a prior art spoon tensioner.

As mentioned above, second tibial contact portion 35 is curved in both the sagittal and coronal planes. Thus, each tooth 39 has a profile or margin that is convexly curved in these planes. In the sagittal plane, teeth 39 are bounded by AL2 to facilitate and not impede insertion of joint distractor 10 into a joint space. In other words, no portion of teeth 39 extend beyond an imaginary boundary extending from and defined by the curvature of first tibial contact portion 33. For example, where first tibial contact portion 33 has a radius of 1.32 in., then the exterior margin of each tooth 39 is either equal to or less then 1.32 in. Where this exterior margin is equal, teeth 39 are then congruent with AL2. This contrasts with teeth 39 extended beyond the boundary defined by AL2 in which introduction of distraction head 30 into a joint space would be more difficult since teeth 39 would dig into the tibia upon their insertion making it difficult to fully insert and seat distraction head 30. However, in the embodiment depicted in which teeth 39 are bounded by AL2, after insertion of distraction head 30, teeth 39 engage and dig into the anterior of a tibia condyle once handle 20 is rotated distally, as shown in FIG. 2. The synovium fluid and cartilage create a very slippery surface. The stabilizing ability of teeth 39 prevents joint distractor 10 from being squeezed or ejected out from the joint space particularly as the surgeon pushes down on handle 20 to lever open the joint space to assess soft tissue laxity. The posterior arrangement of second tibial contact portion 35 relative to first tibial contact portion 33 and its location on the upslope of tibial contact side 32 of distraction head 30 effectively places teeth 39 at the pivot point of joint distractor 10 so that teeth 35 remain engaged to tibia 60 while levering forces are applied to joint distractor 10 (see FIG. 3B) that would ordinarily eject other instruments, such as the osteotome and spoon of FIGS. 1A and 1B, respectively.

As discussed above, femoral and tibial bone contact sides 31, 32 are curved in coronal and sagittal planes. An anatomic sagittal plane generally extends in an anterior-posterior direction and superior-inferior direction relative to a human patient, while an anatomic coronal plane extends in a lateral-medial direction and superior-inferior direction. Reference herein to the sagittal and coronal planes is associated with the preferred application of joint distractor 10 to the human body. As illustrated in FIGS. 3A-3C, distraction head 30 is configured to be introduced into the joint space from an anterior to posterior direction. Thus, the use of the terms sagittal plane and coronal plane are in reference to the preferred application of joint distractor 10 to the human body. However, it should be understood that other embodiments of joint distractor 10 can be configured to be introduced into the joint space from a lateral or medial location, for example. In such embodiment, the joint distractor may appear similar to that of joint distractor 10 but with the curvatures of tibial and femoral contact portions oriented 90 degrees relative to their orientation in joint distractor 10. Nonetheless, such embodiment would have dual curvatures to conform to the dual curvature of the anatomic condyles.

The coronal and sagittal curvatures of distractor head 30 can be determined based on a statistical analysis of a population of femoral and tibial bones in a bone database. One exemplary database is the Stryker Orthopaedics Modeling and Analytics ("SOMA") database, which catalogues various bone morphology datasets relating to size, shape, density, cortical boundaries, location of bony landmarks, and the like, drawn from a collection of individual bones, such as a femur and a tibia. In this regard, the condylar curvatures of a select population of bones (e.g., population based on height, weight, sex, age, and/or the like) in the sagittal and coronal planes can be measured. Such measurements generally fit a normal distribution such that the first, second, and third standard deviations of these measurements for the particularly selected population can be determined. The curvatures of femoral and tibial contact sides of distraction head (e.g., R1 and R2) are then determined to encompass the first, second, or third standard deviation patients in the select population. First standard deviation curvatures may more closely conform to a condyle but exclude about 32% of the patients within the select population. To account for this, multiple joint distractors can be configured to cover the outlier patients to ensure distractor head optimally conforms to a particular patient within that population.

Figure 4A:
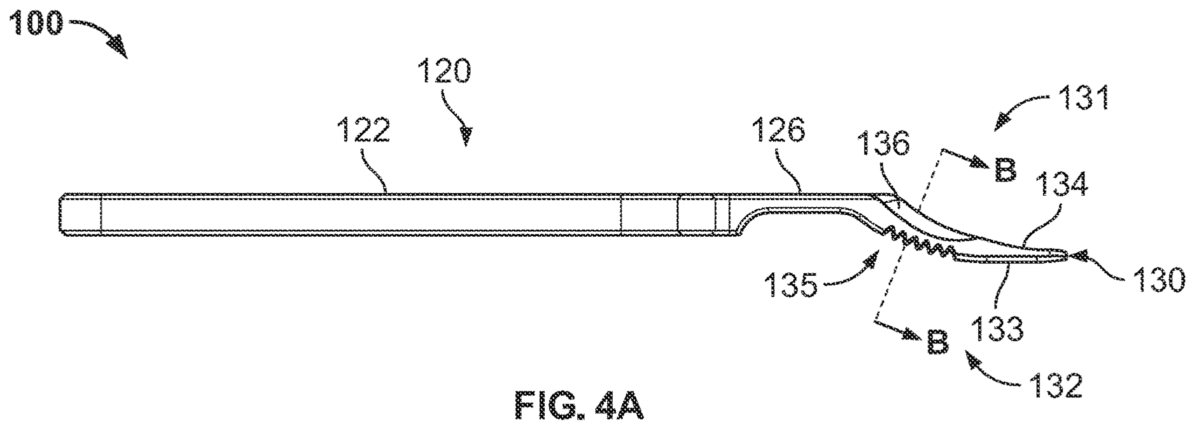
FIG. 4A is a side view of a joint distractor according to another embodiment of the present disclosure.
Figure 4B:
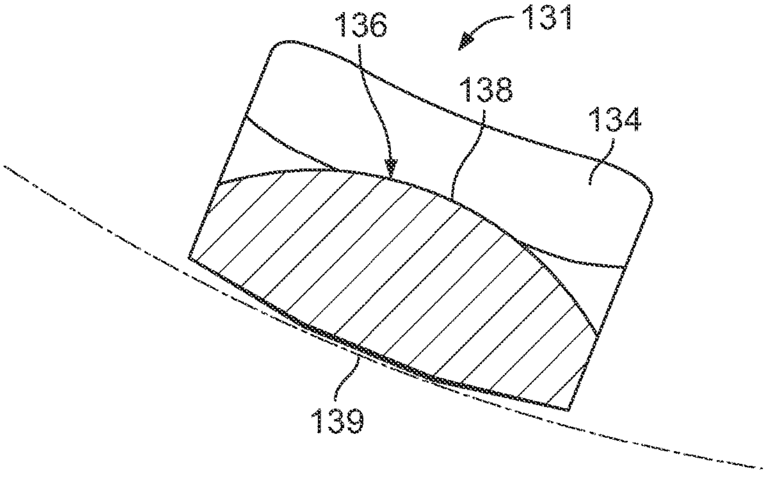
FIG. 4B is a cross-sectional view of the joint distractor of FIG. 4A taken along line B-B thereof.

FIGS. 4A and 4B depict another embodiment joint distractor 100. For ease of review, like elements will be accorded like reference numerals to that of joint distractor 10, but within the 100-series of numbers. In this regard, joint distractor 100 includes a handle 120 with a first portion 122 and a second portion 126 and a distraction head 130 with femoral and tibial contact sides 131, 132. Additionally, femoral bone contact side 131 includes first and second femoral contact portions 134, 136, and tibial contact side 132 includes first and second tibial contact portions 133, 135 that are similarly configured to those of joint distractor 10. However, joint distractor 10 differs in that none of the teeth 139 of second tibial contact portion 135 has a recessed channel. Such configuration may result in single-point contact, rather than two-point contact, for tibial condyles of relatively large size, such as that of curvature C1 in FIGS. 2B and 2D. Thus, while this is an alternative embodiment, this embodiment is not preferred as it is generally more unstable than joint distractor 10 for larger tibial condyles.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A knee joint distractor, comprising:

a handle having a length extending along a longitudinal axis of the knee joint distractor; and a distraction head connected to the handle and extending therefrom, the distraction head having a femoral contact side and a tibial contact side, the femoral contact side having a-first and second femoral contact portions the first femoral contact portion being concavely curved in sagittal and coronal planes, and the second femoral contact portion being convexly curved in the coronal plane, the tibial contact side having first and second tibial contact portions, the first tibial contact portion defining an inferior apex of the tibial contact side, and the second tibial contact portion having a plurality of teeth offset from the inferior apex in a direction toward the handle.

2. The distractor of claim 1, wherein the teeth each extend in a direction transverse to the longitudinal axis of the knee joint distractor.

3. The distractor of claim 2, wherein a length of each tooth is interrupted by a recessed channel.

4. The distractor of claim 3, wherein each tooth includes a first and second edge disposed at opposing sides of the recessed channel.

5. The distractor of claim 4, wherein each tooth includes a third and fourth edge disposed at respective opposed ends thereof.

6. The distractor of claim 1, wherein the tibial contact side is curved in a sagittal plane such that it defines an arc length having a first radius of curvature.

7. The distractor of claim 6, wherein the first tibial contact portion has a curved surface that is congruent with the arc length in the sagittal plane.

8. The distractor of claim 7, wherein the curved surface of the first tibial contact portion is curved in a coronal plane orthogonal to the sagittal plane.

9. The distractor of claim 7, wherein each tooth has a sagittal plane profile that extends no further than the arc length.

10. The distractor of claim 9, wherein the sagittal profile of each tooth is congruent with the arc length.

11. The distractor of claim 1, wherein the second femoral contact portion is concavely curved in the sagittal plane.

12. The distractor of claim 1, wherein the distractor head has first and second ends and is tapered such that a thickness measured between the femoral and tibial contact sides increases from the first end to the second end, the second end being connected to the handle.

13. The distractor of claim 1, wherein the inferior apex extends from a distal tip of the distraction head along a portion of the distraction head.

14. The distractor of claim 1, wherein the first tibial contact portion is absent teeth.

15. A knee joint distractor, comprising:

a handle having a length extending along a longitudinal axis of the knee joint distractor; and a distraction head connected to the handle and extending therefrom, the distraction head having a femoral contact side and a tibial contact side, the femoral contact side having a first femoral contact portion, the tibial contact side having first and second tibial contact portions and an arc length defined by at least the first tibial contact portion having a first radius of curvature, the second tibial contact portion having a plurality of teeth bounded by the arc length such that the teeth do not extend radially beyond the arc length, wherein the teeth each extend in a direction transverse to the longitudinal axis of the knee joint distractor, wherein a length of each tooth is interrupted by a recessed channel.

16. The distractor of claim 15, wherein each tooth includes a first and second edge disposed at opposing sides of the recessed channel.

17. The distractor of claim 16, wherein each tooth includes a third and fourth edge disposed at respective opposed ends thereof.

18. A knee joint distractor, comprising:

a handle having a length extending along a longitudinal axis of the knee joint distractor; and a distraction head connected to the handle and having a femoral contact side having first and second femoral contact portions, and a tibial contact side having a-first and second tibial contact portions, the first tibial contact portion defining an inferior apex of the tibial contact side, the second tibial contact portion having a plurality of teeth offset from the inferior apex in a direction toward the handle, and the first femoral contact portion being concavely curved in a coronal plane, and the second femoral contact portion being convexly curved in the coronal plane, wherein the teeth each extend in a direction transverse to the longitudinal axis of the knee joint distractor, wherein a length of each tooth is interrupted by a recessed channel.

* * * * *